(12) United States Patent
Conte (10) Patent No.: US 7,699,812 B2
(45) Date of Patent: Apr. 20, 2010

(54) SAFETY SYRINGE WITH CAP HOLDING DEVICE

(75) Inventor: Michael Conte, Milltown, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 103 days.

(21) Appl. No.: 10/795,970

(22) Filed: Mar. 8, 2004

(65) Prior Publication Data

US 2004/0199124 A1 Oct. 7, 2004

Related U.S. Application Data

(60) Provisional application No. 60/452,981, filed on Mar. 7, 2003.

(51) Int. Cl.
*A61M 5/32* (2006.01)

(52) U.S. Cl. ............... 604/192; 604/187; 604/110; 604/263

(58) Field of Classification Search ............ 604/187, 604/192–198, 110, 263; 206/365–367; 600/432
See application file for complete search history.

(56) References Cited

U.S. PATENT DOCUMENTS

| 4,742,910 | A | * | 5/1988 | Staebler | 206/365 |
| 4,890,734 | A | * | 1/1990 | Gach | 206/366 |
| 4,955,865 | A | * | 9/1990 | Steiner et al. | 604/192 |
| 5,322,164 | A | | 6/1994 | Richardson et al. | 206/366 |
| 5,356,385 | A | * | 10/1994 | Latini | 604/110 |
| 5,451,214 | A | * | 9/1995 | Hajishoreh | 604/235 |
| 5,540,665 | A | * | 7/1996 | Mercado et al. | 604/145 |
| 5,791,471 | A | | 8/1998 | Radmand | 206/366 |
| 6,780,166 | B2 | * | 8/2004 | Kanda et al. | 604/31 |

OTHER PUBLICATIONS

"Safe-Mate—The Safety Needle for Metal Syringes," safety and compliance description, MedPro, Inc., Mar. 2002 (1 page).
"Safe-Mate—The Safety Needle for Metal Syringes," product description, MedPro, Inc., 2002 (2 pages).
"ScoopCap Safety Needles," JRM Enterprises, 1999 (1 page).
"You'll Feel Safe and Secure With Palmero Heath Care's OSHA Compliance Systems!," product description (1 page).
"Hypo Safety Cartridge Syringe," MPL Technologies (1 page).

* cited by examiner

*Primary Examiner*—Kevin C Sirmons
*Assistant Examiner*—Phillip Gray
(74) *Attorney, Agent, or Firm*—Klauber & Jackson LLC (57) ABSTRACT

A safety syringe and cap holding device for holding a syringe which also allows the syringe to be capped and uncapped while minimizing exposure of the user's hands to the hazard of needle sticks. The cap holding device can be powered electrically or mechanically, and can be selectively operated by a user.

13 Claims, 8 Drawing Sheets

SAFETY SYRINGE WITH CAP HOLDING DEVICE

RELATED APPLICATIONS

This application claims the priority of Provisional Patent Application Ser. No. 60/452,981, filed Mar. 7, 2003, the entire disclosure of which is expressly incorporated herein by reference.

BACKGROUND OF THE INVENTION

1. Field of the Invention

The present invention relates to a device for holding a dental or medical syringe for safe and convenient capping and uncapping of the needle on the syringe.

2. Related Art

The use of needles and syringes in medical and dental applications is widespread. However, the danger of needle sticks inheres in all stages of syringe use, e.g., assembly, uncapping, injection, recapping, disassembly, and discarding. Where deadly diseases can be transmitted by inadvertent needle sticks, the desirability of preventing such inadvertent needle sticks is obvious.

This problem is of particular concern with standard dental and medical safety syringes. Because dental safety syringes are designed to be re-loaded and re-used on the same patient to administer additional doses of anesthetic, where necessary, there is increased exposure of the user's hands to the needle during uncapping and recapping. Further, there is also a risk of exposure of needle sticks from medical syringes during un-capping, use, and re-capping, despite the fact that medical syringes are designed for a single use.

Attempts have been made to design products that provide a "safe" yet easy-to-use method of uncapping and recapping a needle on a syringe. However, many of these products, while offering some advantages, still expose the needle to the user's hands at some point in the assembly or operation, are complicated to assemble, cumbersome to use, or because they include disposable parts, produce excessive medical waste.

For example, "scooping up" the cap using the needle is a recommended method of recapping a needle. An example of a built-in recapper based on the scooping method is the disposable SCOOPCAP manufactured by JRM Enterprises, Inc. and designed for use on standard dental syringes. Although the Scoop Cap is attractive because it requires minimal assembly and produces minimal medical waste, the needle still remains in close proximity to the user's hand during assembly and disassembly, thus affording little protection to the user from needle sticks during these steps.

Another safety needle which fits standard metal syringes is the SAFE-MATE safety needle (MedPro, Inc., Lexington, Ky.) which has a lockable, slidable, protective sheath covering the needle. Although the slidable sheath protects the user's hand during assembly and disassembly of the needle to and from the syringe, and this safety needle produces minimal medical waste, the sheath remains attached to the syringe during use. This disadvantageously impedes access to all areas of the mouth, limiting certain dental procedures such as maxillary posterior injections.

A fully disposable dental syringe assembly has been developed by DENTALOGIC by Protecs Medical Corporation, Miami, Fla. This syringe provides adequate protection from hazard to the user during assembly and capping because the needle is not openly exposed to the user. However, assembly time is excessive, and, although the syringe is designed to be used with one hand, handling the syringe with one hand requires undue manual dexterity. Further, the syringe is not reloadable, which is a disadvantage if another dose of medication is required. Because the syringe is not reloadable, and is totally disposable, excessive medical waste ensues.

Another fully disposable dental syringe assembly, Hypo Safety Cartridge Syringe, has been developed by Dentsply MPL Technologies, Franklin Park, Ill. Although it is pre-assembled, and provides some protection from sticks from the needle when it is attached to the syringe, this syringe assembly still leaves the injection end of the needle exposed during needle uncapping and capping, and therefore still presents a hazard of needle sticks to the user.

Thus, there remains a need for a safe and convenient method for capping and uncapping a standard medical or dental syringe with one hand which requires minimal assembly, has no assembly or disassembly hazard, is reloadable, results in minimal medical waste, and preferably minimizes hand exposure during needle capping and uncapping.

SUMMARY OF THE INVENTION

The present invention relates to a safety syringe and cap holding device comprising a hub for supporting a needle; a cap (or cover) interconnected with the hub, the cover having one or more protrusions for engaging one or more recesses on the hub; a housing having a receptacle for receiving the cap; means in the housing for disengaging the one or more protrusions on the cap from the one or more recesses on the hub to allow the needle to be withdrawn from the cap; and means in the housing for allowing the cap to be withdrawn from the housing. Electronic control of the cap holding device can be provided, wherein the protrusions of the cap can be engaged and disengaged by one or more solenoids or other similar devices.

A method of using a syringe is provided, the method comprising providing a needle assembly including a hub, a needle, and a cover interconnected with the hub and covering the needle; engaging the needle assembly with a syringe body; inserting the needle assembly into a cover holding device; activating the cover holding device to permit the needle to be withdrawn from the cover; using the syringe; reinserting the syringe body and needle into the cover in the cover holding device; and actuating the cover holding device to remove the syringe body, needle assembly, and cover from the cover holding device. The step of activating the cap holding device to permit the syringe and needle to be withdrawn from the cap comprises actuating a switch remote from the needle and the cap holding device.

BRIEF DESCRIPTION OF THE DRAWINGS

Other important objects and features of the invention will be apparent from the following Detailed Description of the Invention taken in connection with the accompanying drawings in which.

DETAILED DESCRIPTION OF THE INVENTION

The present invention relates to a safety syringe and cap holding device. The invention comprises a hub for supporting a needle, a cap (or cover) interconnected with the hub and having one or more protrusions for engaging one or more recesses on the hub, a housing having a receptacle for receiving the cap, means in the housing for disengaging the one or more protrusions on the cap from the one or more recesses on the hub to allow the needle to be withdrawn from the cap, and means in the housing for allowing the cap to be withdrawn from the housing. Electronic control of the cap holding device can be provided, wherein the protrusions of the cap can be engaged and disengaged by one or more solenoids or other similar devices. The safety syringe can be used in any environment where protection from needle sticks is desired, such as in dental and medical environments.

Figure 1:
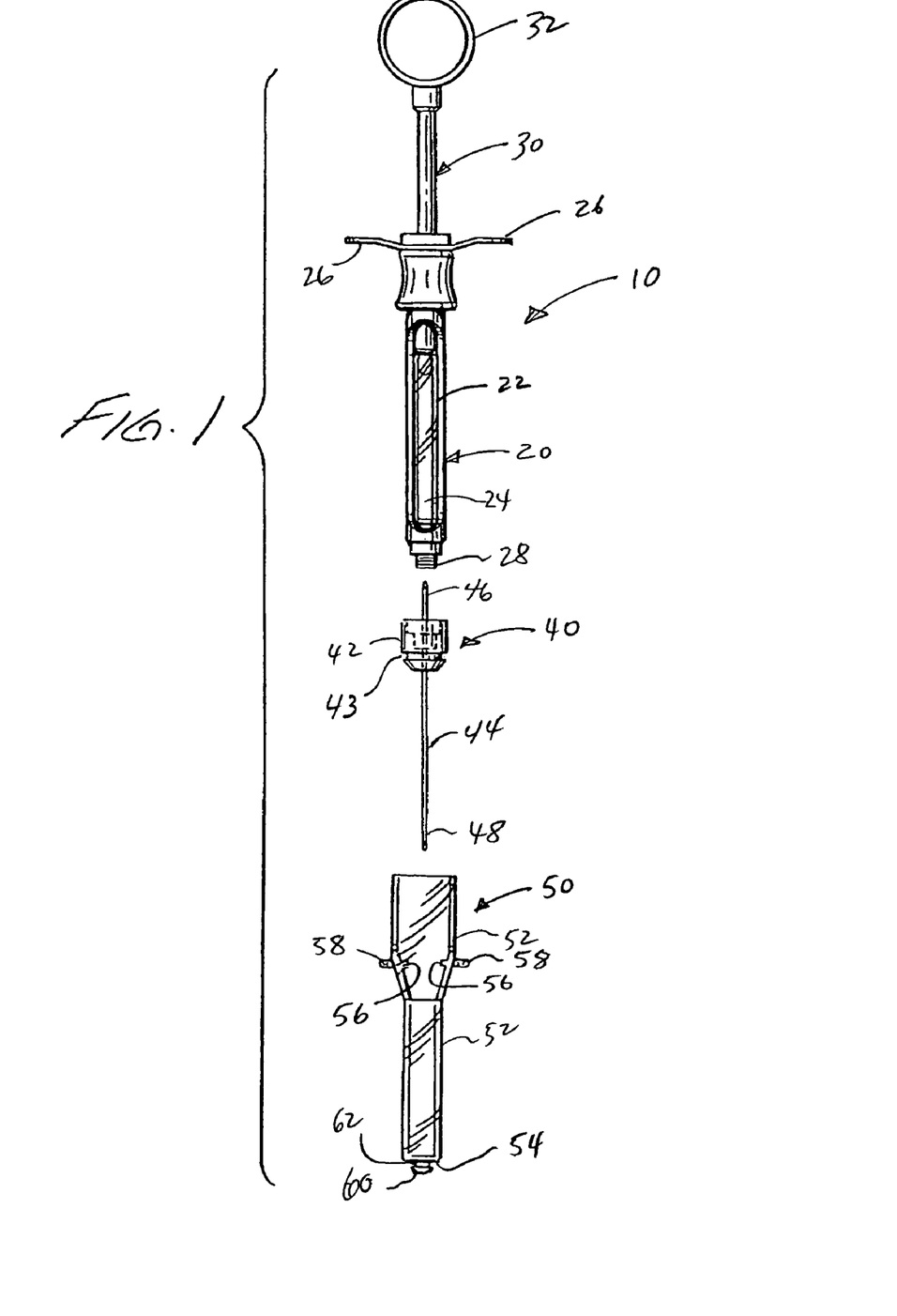
FIG. 1 is an exploded side view of the components of a safety syringe and cap of the present invention.
Figure 2:
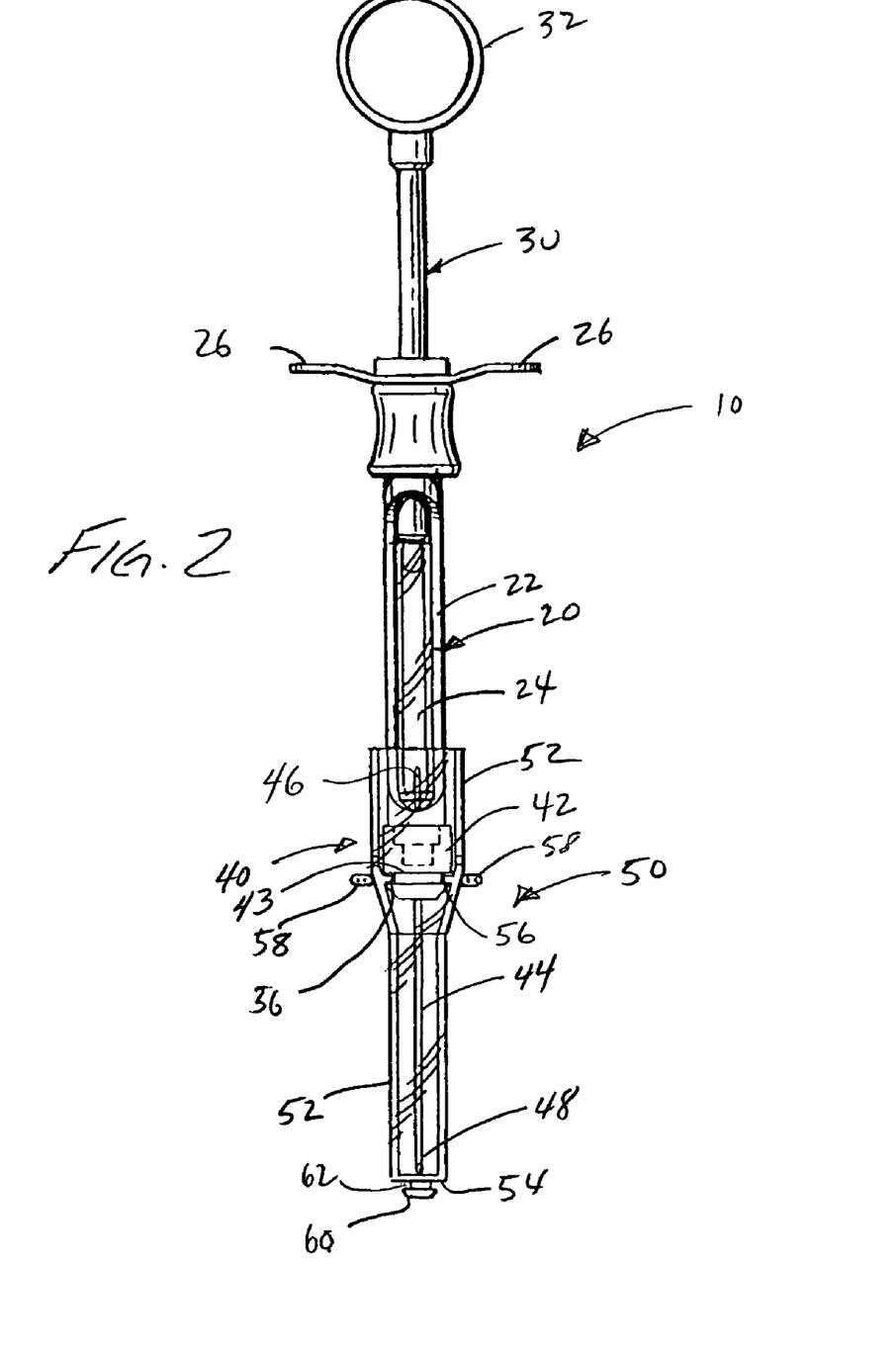
FIG. 2 is a side view of the safety syringe shown in FIG. 1 in assembled form.

A safety syringe and cap according to the present invention is shown in FIGS. 1 and 2. The syringe, generally indicated at 10, includes a cylindrical hollow body 20, a plunger assembly 30, and a needle assembly 40. A cap 50 is configured to cover the needle assembly 40.

A hollow central chamber 22 in the body 20 of the syringe 10 is partially open for receiving a drug cartridge 24 therein. The plunger assembly 30 is moveable through the body 20 and the cartridge 24 to force the contents of the cartridge 24 out through the needle assembly 40. Finger rests 26 extend out from the upper end of the body 20 for allowing a user's fingers to grasp the body 20 while the plunger 30 is actuated by the user's thumb inserted into loop 32. The lower end of the syringe body 20 includes a threaded shaft 28 for engagement with the needle assembly 40.

Needle assembly 40 comprises a hub 42 interconnected with a needle 44. The needle has a cartridge end 46 and an injection end 48. The hub 42 has threads for threadable engagement to the threaded shaft 28 of syringe body 20. The hub includes one or more recesses 43, which may be annular, about an exterior surface. After drug cartridge 24 is inserted into central chamber 22 of the syringe, the needle assembly 40 is attached to the syringe body. The hub 42 is threadably engaged to syringe body 20 causing the cartridge end 46 of needle 44 to pierce the septum of, and extend into, drug cartridge 24.

The cap 50 is positioned over needle assembly 40. The cap 50 is generally cylindrical, being defined by one or more annular walls 52. It is closed at the bottom 54, but is open at the top. The cap 50 is configured to extend about injection end 48 of needle 44, about hub 42 and past the cartridge end 46 of needle 44. The cap 50 can be made of any suitable material, such as plastic, as is generally known in the industry. By covering the injection end 48 and the cartridge end 46 of needle 44, the cap 50 protects against inadvertent needle sticks.

The cap 50 is retained on needle assembly 40 by attachment to hub 42. The cap 50 has one or more internally facing protrusions 56 for engaging the one or more recesses 43 on hub 42. The recess 43 in the hub 42 could be one or more discrete recesses or an annular recess into which one or more corresponding protrusions 56 on the inner wall of the cap 50 can extend. In order to engage and disengage the cap 50 with hub 42, as will be hereinafter described, it is desirable to permit the protrusions 56 to be movable out of engagement with the one or more recesses 43. One way to provide for such movement is to cut away the wall of the cap 50 about the protrusions 56 so that a tab supporting the protrusion 56 remains, the tab being movable with respect to the remainder of the cap wall.

Cap 50 further includes one or more handles 58 on the exterior wall of cap 50 corresponding to the protrusions 56. The handles 58 are used for moving the protrusions 56 into and out of engagement with the one or more recesses 43 of hub 42. Where the protrusions 56 are positioned on tabs, the handles 58 would be positioned on the exterior surfaces of the tabs. Extending from the bottom 54 of cap 50 is end post 60 having a recess 62, the purpose of which will be hereinafter described.

Figure 3:
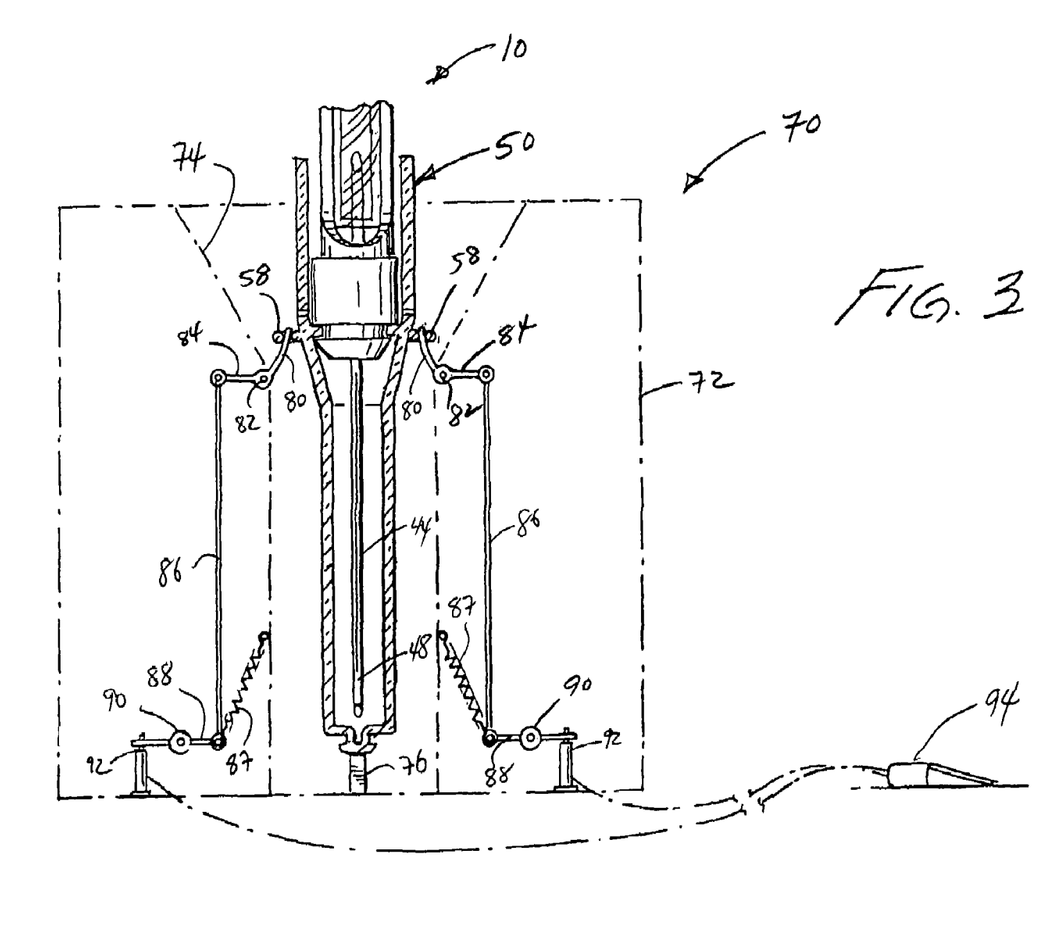
FIG. 3 is a cross-sectional view of a portion of the safety syringe shown in FIG. 2 inserted and locked into a cap holding device of the present invention.

FIG. 3 shows a portion of the syringe 10, having the cap 50 attached thereto, inserted into a cap holding device 70. The cap holding device 70 comprises a housing 72 having a receptacle 74 for receiving the syringe 10 and cap 50 therein. A stop projection 76 is located at the bottom of the receptacle 74. Hooks 80 for engaging cap handles 58 are provided in the receptacle 74. The receptacle 74 and the cap 50 have complimentary geometries to align the cap handles 58 and the hooks 80 when the syringe 10 and cap 50 is inserted into the receptacle 74.

Hooks 80 are components of a linkage system provided within the housing 72 of cap holding device 70. The linkage system can be actuated to move the hooks 80 away from the cap 50, to pull the protrusions 56 to disengage the protrusions 56 from the hub 42 to disengage the cap 50 from the syringe 10. The hooks 80 extend from pivots 82. Arms 84 extend out from pivots 82. Arms 84 are interconnected with vertical rods 86, which are attached at lower ends to levers 88 which sit on fulcrums 90. Pistons 92, which can be actuated by a foot pedal 94 that moves the levers 88 about fulcrums 90 to move vertical rods 86 in a downward direction, pulling down arms 84 and pivoting the hooks 80 radially outward to pull the handles 58 and corresponding protrusions 56 on cap 50 radially to disengage the cap 50 from the syringe 10. The vertical rods 86 are naturally biased, such as by springs 87, in an upward direction so that when the foot pedal 94 is released, the rods 86 move back up and the hooks 80 return the handles 58 and therefore the protrusions 56 to a locking position.

Hooks 80 can merely be rods which engage the handles 58. The handle 58 could be in the form of a ring or the like, having an aperture through which hooks 80 can extend. Alternatively, the hooks could be Y-shaped and the handles could comprise a post received by the Y-shaped hook. A cap or enlargement on the end of the post would allow a Y-shaped hook to bear thereagainst to allow the hook to pull the post.

Figure 4:
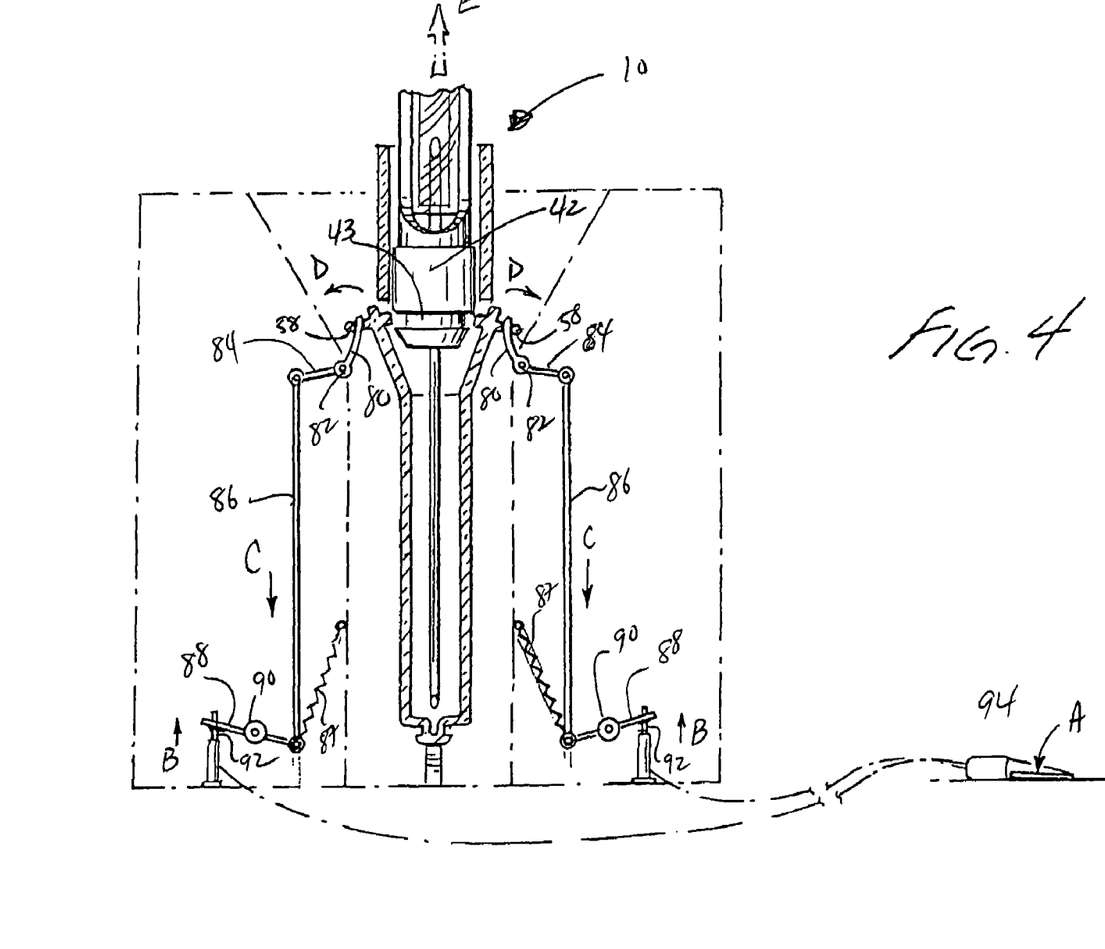
FIG. 4 is a cross-sectional view of a portion of the safety syringe and cap holding device shown in FIG. 3 with the cap unlocked from the syringe.
Figure 5:
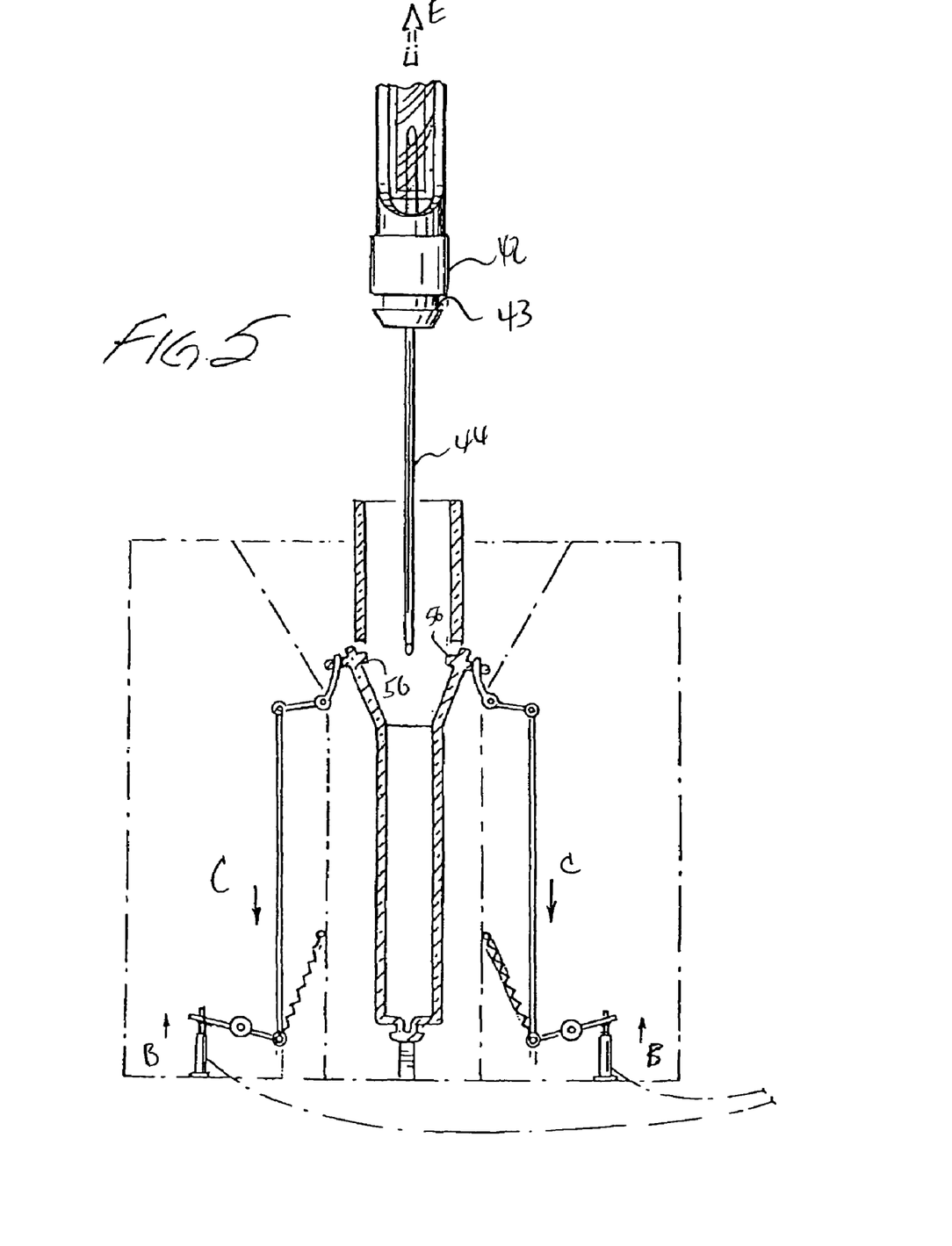
FIG. 5 is a cross-sectional view shown in FIG. 4, with the syringe withdrawn from the cap holding device.

FIGS. 4 and 5 show how the needle 44 on the syringe 10 is unsheathed and re-sheathed. First, a cartridge 24 is loaded into a syringe 10, and the capped needle assembly 40 is attached to syringe body 20. Then the capped syringe 10 is inserted into the receptacle 74 of cap holding device 70. In order to remove the syringe 10 from the holder 70 without the cap (so that the syringe can be used) the foot pedal 94 is actuated, as shown by arrow A, to activate pistons 92 to move them in an upward direction as shown by arrow B. Movement of pistons 92 upward moves levers 88 about fulcrums 90 to pull vertical rods 86 down in the direction of arrows C, against the bias of springs 87. The downward movement of rods 86 pull arms 84 about pivots 82 to move hooks 80 out in the direction indicated by arrows D. Such movement pulls handles 58 to unseat protrusions 56 from the one or more recesses 43 in hub 42. The syringe 10 can then be withdrawn from the housing 72 by moving it in the direction of arrow E, while the cap 50 remains in the housing. The foot pedal 94 can then be released, and the linkage system returns to a locking position.

After the syringe is used, e.g., after injection of the drug into the patient, the syringe is re-inserted into the cap 50 in the housing. The protrusions 56 on the cap engage the one or more recesses 43 on the hub 42. The hub 42 may have a sloped edge leading to the protrusions 56 to cam them back into the one or more recesses 43. In this manner, the syringe can be unsheathed, used, and then re-sheathed in a safe and convenient manner minimizing exposure of a user's hands to the needle.

Figure 6:
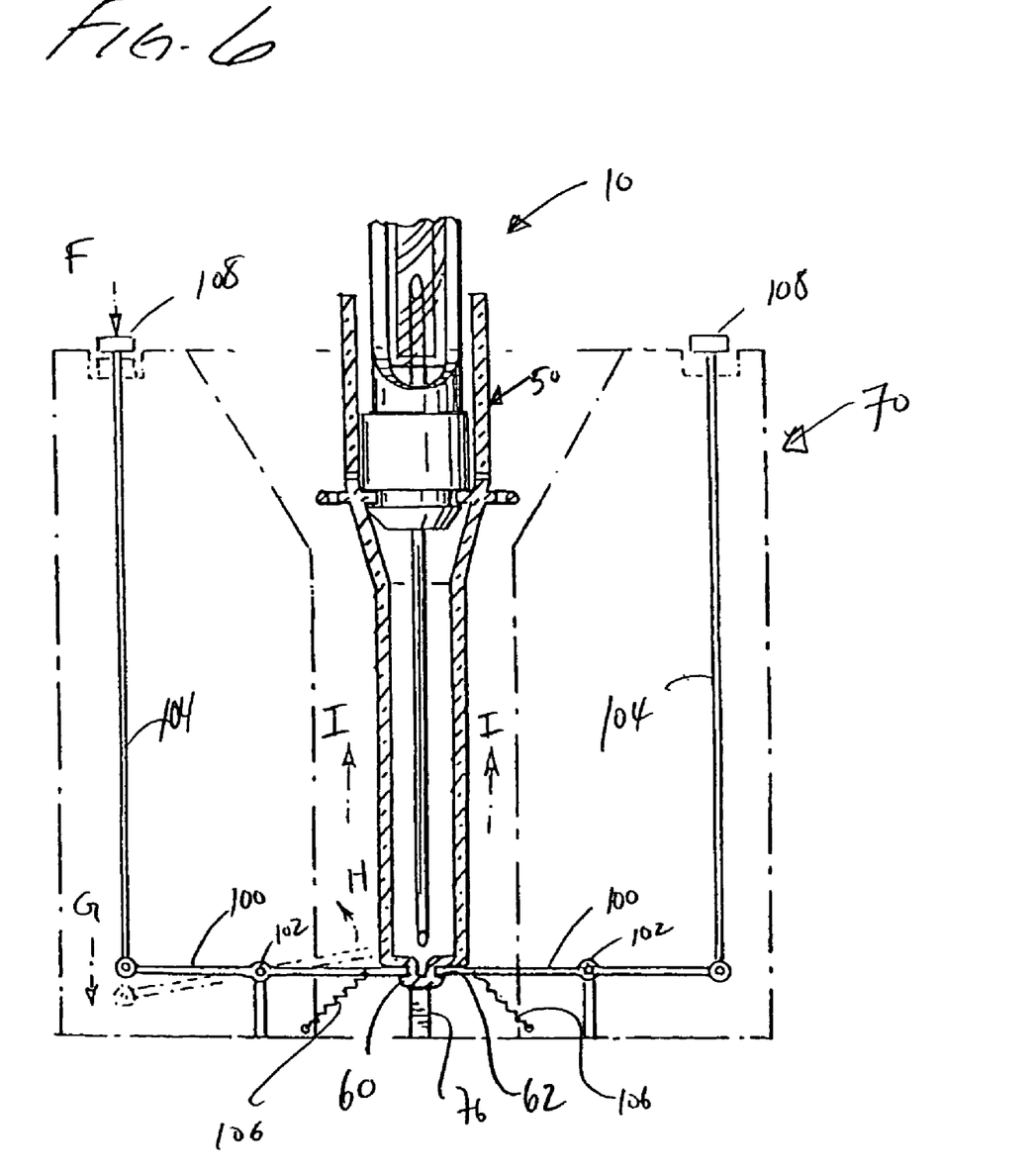
FIG. 6 is a cross-sectional view of a portion of the safety syringe in the cap holding device with the safety syringe and cap being unlocked.
Figure 7:
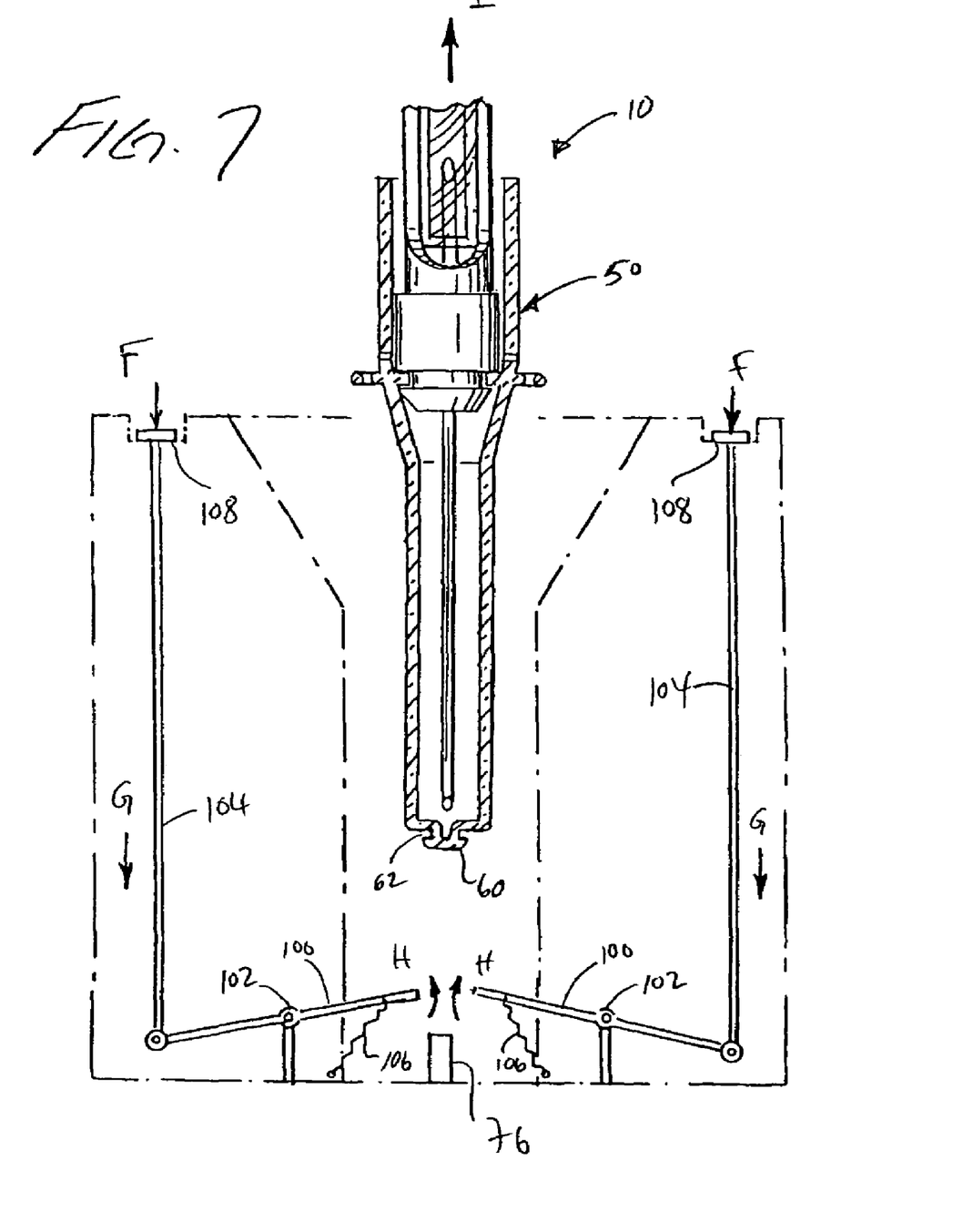
FIG. 7 is a cross-sectional view shown in FIG. 6, with the safety syringe and cap withdrawn from the housing.

FIGS. 6 and 7 show the mechanism for engaging and disengaging the cap 50 in the cap holding device 70. When the syringe 10 is inserted into the cap holding device 70, end post 60 of cap 50 rests on stop projection 76. Engagement levers 100 engage recess 62 at first ends, pass over engagement fulcrums 102, and are interconnected with actuating rods 104 at second ends. Springs 106 bias engagement levers to a horizontal position. Actuating rods 104 are interconnected with release buttons 108 on housing 72 of cap holding device 70.

In order to release the cap 50 from the cap holding device 70, one or more release buttons 108 are actuated in the direction as shown by arrow F, to move actuating rods 104 downward in the direction of arrow G to pivot engagement levers 100 about fulcrums 102 and against the bias of springs 106 to urge the cap 50 and the syringe 10 upward in the direction of arrow H, and out of the cap holding device in the direction of arrow I while disengaging the engagement levers 100 from the recess 62 of post 60.

In summary, the cap holding device of the present invention includes a cap 50 engagable with hub 42 which carries a needle 44 to cover both the cartridge end 46 and injection end 48 of the needle 44. The cover includes internal protrusions 56 which engage one or more recesses 43 on hub 42. The needle assembly 40 can then be attached to the syringe body 20. The cap 50 extends beyond the cartridge end 46 of needle 44 to prevent inadvertent needle sticks during assembly of the syringe 10. Thereafter, the syringe 10 with needle assembly 40 and cap 50 is inserted into the cap holding device 70. In order to remove the needle from the cap, a foot pedal or other actuating device is utilized. Importantly, the foot pedal or actuating device is remote from needle 44 and allows one to remove the needle from the cap without the need to position ones hands in proximity to the needle, thereby minimizing inadvertent sticks. After use, the syringe can be inserted back into the cap that has been retained in the cap holding device. Again, one does not need to position ones hands proximate the needle during this process, thereby minimizing the risk of inadvertent needle sticks.

When one is finished using the syringe, the syringe and cap can be removed from the cap holding device by actuating another button or other actuating device. Because the cap covers the needle, inadvertent needle sticks are prevented. Thereafter, the needle assembly 40 can be disconnected from the syringe 10 and discarded. Because the cap covers the cartridge end and injection end of the needle during this process, inadvertent needle sticks are prevented.

It may be desirable for the configuration of the cap to be keyed to the receptacle in the cap holding device to provide for alignment of the cap in the cap holding device so that the hooks engage the handles. Additionally, it should be noted that the construction of the hooks, handles and the attachment of the cap to the hub could be varied as desired. For example, the cap could have opposing internally facing protrusions that engage a recess in a hub and rather than providing handles on the cap, the cap could be pinched to deform the shape of the cap sufficiently to allow the protrusions to disengage from the hub. Other manners of constructing the hub, cap and housing are considered to be within the scope of the invention. The housing may be weighted by use of a heavy or weighted material, such as a metal, such as lead or the like. The weighted material can be used in the construction of the housing or can be placed into the housing for anchoring and stabilizing the device.

Figure 8:
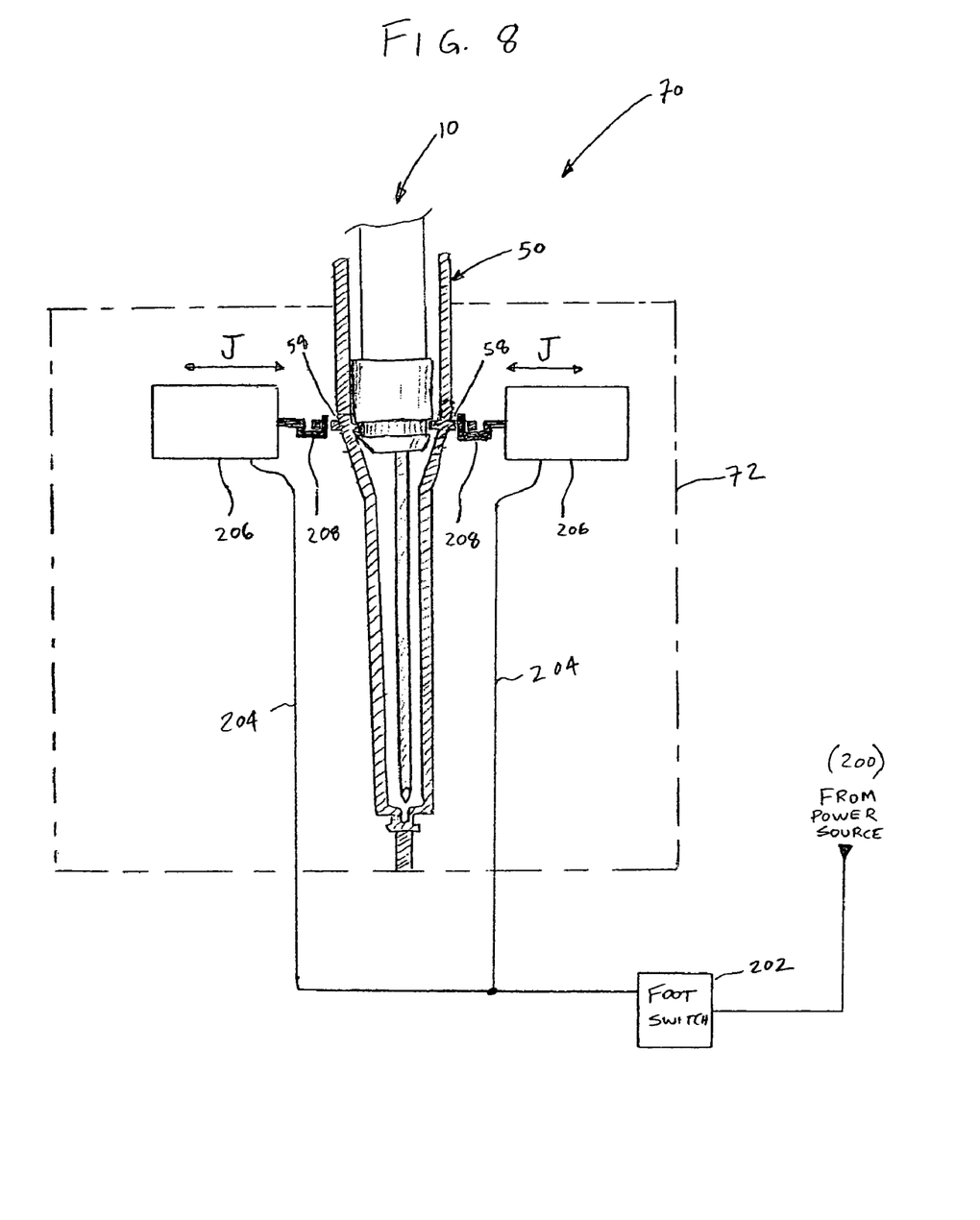
FIG. 8 is a view showing an alternate embodiment of the cap holding device of the present invention, wherein electronic control is provided.

FIG. 8 is a view showing an alternate embodiment of the cap holding device 70 of the present invention, wherein electronic control is provided. A pair of solenoids 206 are positioned perpendicular to the longitudinal axis of the syringe 10, and include hooked engagement members 208 for engagement with the handles 58 of the cap 50. The hooked engagement members 208 are interconnected with the solenoids 206, and move laterally in the direction indicated by arrows J. When a user depresses the foot switch 202, electrical current is sent from the power source 200 to solenoids 206 via connections 204. The current causes an electromotive force to be generated by the solenoids 206, which, in turn, pull the engagement hooks 208 toward the solenoids 206. This causes the protrusions 56 of the cap 50 to move away from the syringe, allowing same to be removed from the cap 50 while the cap 50 is retained in the holding device 70. The solenoids 206 could be of any type or manufacture that provides sufficient force to pull the handles 58 and urge the protrusions 56 away from the syringe 10. After the syringe has been removed from the cap, the foot switch 202 is opened, causing current to cease flowing to the solenoids 206 and engagement members 208 to return to their original positions. The power source 200 could be any alternating (AC) or direct current (DC) power source. Any other electronic means for operating the cap holding device 70, such as a motor-driven mechanism, is considered within the scope of the present invention.

The embodiment shown in FIG. 8 could also include a mechanism for engaging and disengaging the cap 50 with the holding device 70, such as the mechanism discussed earlier with reference to FIGS. 6-7. It should be noted that this mechanism could also be modified to be operated electrically, wherein one or more solenoids are provided for engaging and disengaging the end post 60 of the cap 50. Such an arrangement would work in conjunction with the electronic control mechanism of FIG. 8 to provide an entirely electrically operated device.

Having thus described the invention in detail, it is to be understood that the foregoing description is not intended to limit the spirit and scope thereof.

What is desired to be protected by Letters Patent is set forth in the appended claims.

What is claimed is:

1. A safety syringe and cap holding device comprising:
   a syringe having a body portion and a needle assembly interconnected with the body portion, the needle assembly including a needle with an injection end and a hub, the hub including at least one recess disposed annularly about the hub;
   a cap removably attached to the hub and covering the injection end of the needle, the cap including at least a pair of opposing protrusions for engagement with the at least one recess of the hub;
   a cap holding device having a receptacle for receiving the cover;

disengagement means in the cap holding device for disengaging the at least a pair of opposing protrusions from engagement with the at least one recess of the hub by pulling the protrusions radially outwardly to detach the cap from the hub to allow the syringe and needle assembly to be withdrawn from the cap holding device with the injection end of the needle uncovered while the cap remains in the cap holding device; and a mechanical linkage system in the cap holding device for selectively retaining or releasing the cap from engagement within the cap holding device.

2. The apparatus of claim 1, wherein the disengagement means comprises one or more hooks for engaging one or more handles on the cap for disengaging the at least pair of opposing protrusions away from the at least one recess to disengage the cap from the hub.

3. The apparatus of claim 1, wherein the disengagement means is actuated remotely from the cap holding device.

4. The apparatus of claim 1, wherein the disengagement means includes one or more solenoids in the cap holding device for moving one or more hooks for engaging one or more handles on the cap for disengaging the at least pair of opposing protrusions from the at least one recess to disengage the cap from the hub.

5. The apparatus of claim 4, wherein the plurality of solenoids are actuated remotely from the cap holding device.

6. The apparatus of claim 1, wherein the mechanical linkage system comprises one or more solenoids having one or more hooks for engaging and disengaging the cap in the cap holding device.

7. The apparatus of claim 1 wherein the cap holding device comprises a weighted base.

8. A safety syringe and cap holding device comprising:
a syringe having a body portion and a needle assembly interconnected with the body portion, the needle assembly including a needle with an injection end and a hub;
a cap removably attached to the hub and covering the injection end of the needle, the cap including one or more protrusions extending radially inward of the cap into engagement with the hub and one or more handles corresponding to the one or more inwardly facing protrusions;
a cap holding device having a receptacle for receiving the cap; and disengagement means in the cap holding device for disengaging the one or more protrusions by pulling the handles radially outwardly with respect to the hub to detach the cap from the hub and retaining the cap in the cap holding device to allow the syringe and needle assembly to be withdrawn from the cap holding device with the injection end of the needle uncovered while the cap remains in the cap holding device, the disengaging means for disengaging the cover comprising one or more hooks in the receptacle for engaging the one or more handles to move the one or more internally facing protrusions radially outwardly out of engagement with the hub.

9. The apparatus of claim 8, wherein each of the one or more handles is substantially oval and includes an interior opening.

10. The apparatus of claim 9, wherein the cap includes at least a pair of opposing handles.

11. The apparatus of claim 8, wherein the one or more hooks is sized to extend through the one or more handles.

12. A safety syringe and cap holding device comprising:
a syringe having a body portion and a needle assembly interconnected with the body portion, the needle assembly including a needle with an injection end and a hub having a recess formed therein;
a cap removably attached to the hub and covering the injection end of the needle, the cap having a protrusion for engagement with the recess of the hub;
a cap holding device comprising a housing having a receptacle for receiving the cap;
a disengagement means in the cap holding device for disengaging the cap from the hub by pulling the protrusion radially outwardly from the recess and retaining the cap in the cap holding device to allow the syringe and needle assembly to be withdrawn from the cap holding device with the injection end of the needle uncovered while the cap remains in the cap holding device; and
an actuator positioned remotely from the housing for actuating the disengagement means within the cap holding device.

13. The apparatus of claim 12, wherein the actuator is not integrally attached to the housing.

* * * * *